United States Patent [19]

Mares et al.

[11] 4,213,906

[45] Jul. 22, 1980

[54] HYDROGEN PEROXIDE OXIDATION PROCESS FOR KETONES

[75] Inventors: Frank Mares, Whippany; Stephen E. Jacobson, Succasunna, both of N.J.

[73] Assignee: Allied Chemical Corporation, Morris Township, Morris County, N.J.

[21] Appl. No.: 926,778

[22] Filed: Jul. 21, 1978

[51] Int. Cl.$^2$ .................................................. C07D 313/04
[52] U.S. Cl. ................................... 260/343; 260/343.5
[58] Field of Search ............................... 260/343, 343.5

[56] References Cited

U.S. PATENT DOCUMENTS 3,590,080  6/1971  Beesley ............................. 260/343

FOREIGN PATENT DOCUMENTS 44-10243  5/1969  Japan ............................. 260/343
45-2728   1/1970  Japan ............................. 260/343

*Primary Examiner*—Henry R. Jiles
*Assistant Examiner*—Jane T. Fan
*Attorney, Agent, or Firm*—R. A. Harman; H. M. Kasper

[57] ABSTRACT

A process for oxidizing ketones with hydrogen peroxide. The ketone is contacted with the hydrogen peroxide in a buffered solution in the presence of an arsenic containing catalyst. This process can lead to lactones directly from cyclic ketones.

3 Claims, No Drawings

HYDROGEN PEROXIDE OXIDATION PROCESS FOR KETONES

BACKGROUND OF THE INVENTION

Cyclic ketones are oxidized to lactones or hydroxy acids with peracids in the Baeyer-Villinger reaction and such peracids include persulfuric, perbenzoic, perphthalic, peracetic and trifluoroperacetic acid. In some instances peracids can be substituted by concentrated (90%) $H_2O_2$ and carboxylic acid anhydride.

S. Kamimura in Japan Pat. No. 2728/1970 dated Jan. 29, 1970 discloses a method for making 6-hydroxycaproic acid or its derivative by decomposition of cyclohexanone peroxides in the presence of arsenic catalysts.

S. Kamimura in Japan Pat. No. 10243-1969 issued May 13, 1969 discloses a method for making esters by oxidation of ketones with hydrogen peroxide in the presence of organic and inorganic arsenic compounds. Employing $H_2O_2$ as the oxidant, this reference gives 6-hydroxycaproic acid as the main product. In the presence of secondary alcohols such as cyclohexanol the lactone was solvolysed to the corresponding alkyl 6-hydroxy caproate resulting in a low yield of lactone.

SUMMARY OF THE INVENTION

It is a purpose of the invention to provide an improved method for the oxidation of ketones.

It is another purpose of the invention to provide an improved method for the preparation of lactones or esters by oxidation of ketones by preventing lactone or ester solvolysis by such agents as water, the byproduct of the oxidation, or by secondary alcohols present in the reaction mixture.

A solution of ketone is contacted with hydrogen peroxide in the presence of a catalyst comprising arsenic as such or as an arsenic compound wherein a buffering agent is added to the solution to decrease the protonic acidity caused by the arsenic acid or its derivatives. The buffer comprises a base in an amount of between about 0.5 and 3 equivalents with respect to the equivalents of arsenic derivatives employed. The buffering agent suppresses the hydrolysis of the oxidation products.

DETAILED DESCRIPTION OF THE INVENTION

Ketones can be oxidized to esters or to a mixture of alcohols and carboxylic acids by $H_2O_2$ in the presence of catalytic quantities of arsenic compounds. Cyclic ketones can be oxidized to a mixture of lactones and hydroxyacids by $H_2O_2$ in the presence of catalytic quantities of arsenic compounds. Arsenic compounds include arsenic as such or arsenic derivatives, preferably derivatives having hydroxy groups or forming such groups during the reaction. Aryl alkyl ketones react with $H_2O_2$ in the presence of catalytic quantities of arsenic compounds to give phenol carboxylates or phenol and carboxylic acids.

We have found that employing buffers of a concentration between about 0.5 and 3 equivalent for each equivalent of acidic hydrogen in the arsenic acid derivative and preferably of a concentration between about 0.8 and 1.5 equivalent for each equivalent arsenic acid derivative in the solution decreases the rate of lactone and ester solvolysis and the polymerization of lactone to polyester. Such buffers include salts formed from bases and weak acids or bases themselves.

Suitable acids for forming the buffering salt employed include acetic acid, propionic acid, butyric acid, isobutyric acid, valeric acid, caproic acid, chloroacetic acid, dichloroacetic acid, bromoacetic acid, 2-chloropropionic acid, hexahydrobenzoic acid, picolinic acid, nicotinic acid, benzoic acid, o-toluic acid, m-toluic acid, p-toluic acid, alpha-naphthoic acid, beta-naphthoic acid, phenylacetic acid, m-chlorobenzoic acid, p-chlorobenzoic acid, o-nitrobenzoic acid, m-nitrobenzoic acid, p-nitrobenzoic acid, succinic acid, glutaric acid, adipic acid, pimelic acid, phthalic acid, o-phenylene diacetic acid, and boric acid.

Suitable bases for forming the buffering salt employed include ammonium hydroxide, lithium hydroxide, tetramethylammonium hydroxide, and aromatic bases such as pyridine, quinoline.

A buffering agent may also be provided by zwitterions of aromatic bases containing carboxylic groups such as picolinic acid. The bases composing the buffering agents are limited to such bases which form soluble salts with arsenic derivatives.

Preferred buffering agents include lithium acetate, picolinic acid, ammonium acetate, tetramethylammonium acetate.

Solvents for the reaction include secondary alcohols, ethers and nitriles such as isopropanol, dioxane, ether, cyclohexanol, acetonitrile, propionitrile, benzonitrile.

The reaction temperature is not critical and can be between about 50° C. and 90° C.

The reaction mixture can be continually analyzed with gas chromatography and at the end of the reaction with nuclear magnetic resonance. Biphenyl is convenient as an internal standard for the oxidation of cyclic ketones.

An advantage in the use of buffers is the decrease or prevention of lactone hydrolysis such as would result from the presence of the by-product water or from alcoholysis when secondary alcohols are present in the mixture.

The resulting lactones are useful as starting materials for the production of lactams and polymers such as polyamides.

EXAMPLE 1

Oxidation of a Mixture of Cyclohexanone and Cyclohexanol in the Presence of Picolinic Acid A mixture of cyclohexanone (30.6 mmol), cyclohexanol (30 mmols), As(OEt)$_3$ (1.5 mmol), picolinic acid (0.105 g, i.e. 0.85 mmol, buffer), biphenyl (internal standard, 0.401 g) and acetonitrile (10.67 ml) was heated to 80° and then a mixture of $H_2O_2$ (30.7 mmol) and acetonitrile (3.87 g) was added in 3 hours. The reaction mixture was periodically analyzed by g.c. and at the end of the reaction by nmr. The content of cyclohexanol remained constant while the concentration of cyclohexanone gradually decreased. The maximum selectivity of caprolactone (98.7%) was obtained after 5.5 hours. Then the yield of caprolactone started to decrease due to hydrolysis to 6-hydroxycaproic acid. At the end of the reaction the mixture contained unreacted cyclohexanol (30 mmol), cyclohexanone (10.91 mmol), caprolactone (13.36 mmol), 6-hydroxycaproic acid (1.9 mmol), oligomeric esters (2.6 mmols). No cyclohexyl 6-hydroxy caproate was formed.

EXAMPLE 2

Oxidation of Cyclohexanone by H₂O₂ in the Presence of Buffers

The procedure corresponded to the procedure disclosed in Example 1, except that no cyclohexanol was present and the buffering agent was either lithium acetate, ammonium acetate or tetramethylammonium hydroxide. The results are summarized in Table I.

Table I

| | | | | | | 6-hydroxy | Oligomeric | Recovered | | Selectivity | Total Selectivity to Lactone |
|---|---|---|---|---|---|---|---|---|---|---|---|
| Sample | Ketone mmol | $H_2O_2$ mmol | Catalyst | Time hr. | Lactone % | caproic acid % | esters % | Ketone % | $H_2O_2$ % | To Lactone % | and its Derivatives |
| | Cyclohexanone | | | | | | | | | | |
| 1 | 30.6 | 23.78 | As(OEt)₃ | 5.42 | 44 | — | — | 25.3 | 18 | 58.9 | — |
| | | | | 23.4 | 27.3 | 25.6 | 22.4 | 25.3 | 0 | 36.5 | 100 |
| 2 | 30.6 | 31 | As₂O₅ | 4 | 32.7 | — | — | 35.3 | 5 | 51 | |
| | | | | 9 | 24 | 24.8 | 14.7 | 35.3 | 1 | 37 | 98 |
| | Buffers | | | | | | | | | | |
| | | | 1 mole of LiOAC/1 mole of As | | | | | | | | |
| 3 | 30.6 | 31.27 | As(OEt)₃ | 5 | 51 | — | — | 17.7 | 19 | 62 | — |
| | | | | 12 | 50 | 33 | 8 | 11 | — | 56 | 100 |
| | | | 0.5 mole of picolinic acid/1 mole of As | | | | | | | | |
| 4 | 30.6 | 30.75 | As(OEt)₃ | 4.7 | 52 | — | — | 16.3 | 20 | 62.1 | |
| | | | | 10.5 | 37 | 39.4 | 18.3 | 5.7 | 4 | 39.2 | 99 |
| | | | 3 moles of NH₄⁺OAC/1 mole of As | | | | | | | | |
| 5 | 30.6 | 31 | As₂O₅ | 4 | 35.6 | 9 | — | 52 | 21 | 74.2 | 96.6 |
| | | | 3 moles of (CH₃)₄N⁺OH⁻/1 mole of As | | | | | | | | |
| 6 | 30.6 | 30.6 | As₂O₅ | 5 hr. | 40 | — | — | 46 | — | — | |
| | | | | 9 | 46 | 9 | 0 | 42 | 26 | 79.3 | 97 |

We claim:

1. In a method for oxidizing a solution of cyclic ketone to obtain lactone with hydrogen peroxide in the presence of a catalyst comprising a member of the group consisting of arsenic as such or as an arsenic compound, the improvement which comprises addition to the solution of between about 0.5 to 3 equivalents of a buffering agent with respect to the equivalents of arsenic derivative employed, said buffering agent comprising salts of weak acids and bases or bases which form soluble salts with arsenic derivatives themselves, thereby suppressing the hydrolysis of the oxidation products.

2. The improved process as set forth in claim 1 wherein the buffering is effected by addition to the solution of a member of the group consisting of tetramethylammonium hydroxide, lithium acetate, picolinic acid, ammonium acetate.

3. The improved process as set forth in claim 1 wherein between about 0.8 and 1.5 equivalent of buffering agent is employed.

* * * * *